(12) United States Patent
Irazoqui et al.

(10) Patent No.: US 8,475,374 B2
(45) Date of Patent: Jul. 2, 2013

(54) INTRA-OCCULAR PRESSURE SENSOR

(75) Inventors: Pedro P. Irazoqui, Lafayette, IN (US); Eric Y. Chow, Colorado Springs, CO (US); William J. Chappell, West Lafayette, IN (US); Chin-Lung Yang, Tainan (TW); Babak Ziaie, W. Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 308 days.

(21) Appl. No.: 12/196,534

(22) Filed: Aug. 22, 2008

(65) Prior Publication Data

US 2009/0069648 A1 Mar. 12, 2009

Related U.S. Application Data

(60) Provisional application No. 60/957,477, filed on Aug. 23, 2007, provisional application No. 61/012,232, filed on Dec. 7, 2007.

(51) Int. Cl.
*A61B 5/00* (2006.01)

(52) U.S. Cl.
USPC .......................................... 600/398

(58) Field of Classification Search
USPC .............. 600/302, 318, 561, 398–400; 604/8, 604/9; 608/107
See application file for complete search history.

(56) References Cited

U.S. PATENT DOCUMENTS

| | | | | |
|---|---|---|---|---|
| 4,922,913 | A * | 5/1990 | Waters et al. | 600/398 |
| 6,083,174 | A | 7/2000 | Brehmeier-Flick et al. | |
| 6,443,893 | B1 * | 9/2002 | Schnakenberg et al. | 600/398 |
| 6,464,687 | B1 * | 10/2002 | Ishikawa et al. | 604/891.1 |
| 6,579,235 | B1 * | 6/2003 | Abita et al. | 600/398 |
| 6,890,300 | B2 * | 5/2005 | Lloyd et al. | 600/398 |
| 6,939,299 | B1 | 9/2005 | Petersen et al. | |
| 2003/0225318 | A1 | 12/2003 | Montegrande et al. | |
| 2006/0173259 | A1 * | 8/2006 | Flaherty et al. | 600/331 |
| 2007/0023758 | A1 | 2/2007 | Tsurume et al. | |
| 2007/0123767 | A1 * | 5/2007 | Montegrande et al. | 600/398 |
| 2009/0203985 | A1 * | 8/2009 | Ehrecke | 600/398 |

FOREIGN PATENT DOCUMENTS

| | | |
|---|---|---|
| EP | 0981293 B1 | 10/2002 |
| EP | 1694205 A1 | 8/2006 |
| WO | 2005048835 A1 | 6/2005 |

OTHER PUBLICATIONS

PCT Search Report dated Nov. 3, 2008 of Patent Application No. PCT/US08/73987 filed Aug. 22, 2008.

Eggers, T. et al., "Advanced Hybrid Integrated Low-Power Telemetric Pressure Monitoring System for Biomedical Applications", IEEE, 2000, pp. 329-334.

Lizon-Martinez, Santiago et al., "Design of a System for Continuous Intraocular Pressure Monitoring", IEEE, 2005, 7 pages.

Flick, Bernd B. et al., "A Portable Microsystem-Based Telemetric Pressure and Temperature Measurement Unit", IEEE, 2000, 5 pages.

(Continued)

*Primary Examiner* — Max Hindenburg

(74) *Attorney, Agent, or Firm* — Maginot, Moore & Beck

(57) ABSTRACT

A system is provided for monitoring intraocular pressure, the system comprising: a sensor package configured to be disposed in the suprachoroidal space of a patient's eye; a pressure sensor; a wireless transceiver disposed within the sensor package and coupled to the pressure sensor; an external transceiver, the external receiver being wirelessly coupled to the wireless transceiver when the transceiver is disposed proximate to the patient's eye.

16 Claims, 19 Drawing Sheets

OTHER PUBLICATIONS

Najafi, Nader et al., "Initial Animal Studies of a Wireless, Batteryless, MEMS Implant for Cardiovascular Applications", Biomedical Microdevices, 2004, pp. 61-65.

Rizq, Raed N. et al., "Intraocular Pressure Measurement at the Choroid Surface: A Feasibility Study with Implications for Implantable Microsystems", British Journal of Ophthalmology, 2001, 5 pages.

Pan, Tingrui et al., "Modeling and Characterization of a Valved Glaucoma Drainage Device with Implications for Enhanced Therapeutic Efficacy", IEEE, 2005, 4 pages.

Liu, John H.K. et al., "Twenty-Four-HOur Intraocular Pressure Pattern Associated with Early Glaucomatous Changes", Investigative Ophthalmology & Visual Science, Apr. 2003, pp. 1586-1590, vol. 44, No. 4.

Vittoz, Eric A., "Very Low Power Circuit Design: Fundamentals and Limits", IEEE, 1993, pp. 1439-1442.

Vilches, Antonio et al., "Analogue Micropower FET Techniques Review", Semiconductor Science and Technology, 2004, pp. R19-R34.

Evans, David W. et al., "Spectral Content of the Intraocular Pressure Pulse Wave: Glaucoma Patients Versus Normal Subjects", Graefe's ARch Clin Exp Ophthalmo., 2002, pp. 475-480.

Third Party Submission dated Aug. 13, 2012 of EP Patent Application No. 08798465.4 filed Aug. 22, 2008, 13 pages.

* cited by examiner

INTRA-OCCULAR PRESSURE SENSOR

CROSS REFERENCE TO RELATED APPLICATIONS

This application claims benefit of U.S. Provisional Application No. 60/957,477, filed Aug. 23, 2008, and also U.S. Provisional Application No. 61/012,232 filed Dec. 7, 2007. These applications are hereby incorporated by reference for all purposes.

FIELD OF THE INVENTION

The invention relates to intra-ocular pressure sensors, and more particularly, to a wireless and inductively powered intra ocular pressure sensor for configured implantation in a patient's eye.

BACKGROUND OF THE INVENTION

The use of wireless sensing for monitoring an individual's physiological parameters has been gaining interest in recent years. The shift towards wireless sensing and away from traditional tethered measurement procedures performed at healthcare facilities may be attributed to the numerous potential benefits associated with wireless based recordings. Such benefits include improvement of patients' quality of life, elimination of periodic costs associated with testing at healthcare facilities, decreased risk of infection, and the possibility of earlier detection of health-status degradation.

Wireless sensing has shown potential benefits for the continuous-time measurement of physiological data. One such application is the recording of intraocular pressure (IOP) for patients with glaucoma. Real-time, continuous and accurate intra-ocular pressure recordings will provide a substantial improvement in the quality of care provided to glaucoma patients, as significant changes in IOP can occur in a period of hours or even minutes. Real-time, continuous monitoring will greatly improve the quality of care provided to glaucoma patients through accurate pressure monitoring, providing the opportunity for complete management of the disease progression.

Ultra-low-power circuits facilitate the use of inductively-coupled power for implantable wireless systems, enabling real-time continuous monitoring of physiologic signals. Compact circuit size is also desirable for implantable sensor systems.

What is needed, therefore, are techniques for wirelessly monitoring intra-ocular pressure.

SUMMARY OF THE INVENTION

For widespread use of wireless IOP sensing to occur, new system architectures that meets the low-power and size constraints, dictated by wireless power schemes and implant area, respectively, are desired. One embodiment of the present invention provides the design and fabrication of a compact, nanopowered operational amplifier for continuous recording of IOP signals in vivo.

One embodiment of the present invention provides an active, implantable system for monitoring pressure, the system having: a sensor package configured to be disposed in a human body; a pressure sensor; a wireless transceiver disposed within the sensor package and coupled to the pressure sensor; an external transceiver, the external receiver being wirelessly coupled to the wireless transceiver when the transceiver is disposed proximate to the patient's eye; and a wireless power supply disposed externally to the patient's body.

Another embodiment of the present invention provides such a system wherein the wireless power supply comprises an inductive power supply.

A further embodiment of the present invention provides such a system further having a coil disposed within the sensor package, wherein a current is induced by a second coil disposed externally to the human body.

Yet another embodiment of the present invention provides such a system wherein the wireless power supply is a radio frequency receiver, configured to receive radio frequency transmissions from an external base station and convert the radio frequency transmissions into electrical current.

A yet further embodiment of the present invention provides such a system wherein the wireless radio frequency receive provides an antenna, the antenna being configured for the transmission of data and the transmission of power Still another embodiment of the present invention provides such a system further having a power storage unit.

A still further embodiment of the present invention provides such a system wherein the power storage unit is a capacitor.

Even another embodiment of the present invention provides such a system wherein the power storage unit is a battery.

An even further embodiment of the present invention provides such a system wherein the sensor package actively monitors pressure within the human body stores data collected by the monitoring and transmits the data either simultaneously or at a desired interval.

Even yet another embodiment of the present invention provides such a system wherein the monitoring is either periodic or continuous.

An even yet further embodiment of the present invention provides such a system, the system being configured to be disposed within the eye of the human body.

Still yet another embodiment of the present invention provides such a system wherein the system is configured to be disposed within the suprachoroidal space of the eye of the human body.

A still yet further embodiment of the present invention provides such a system further having a biocompatible package wherein the sensor, RF antenna, and associated circuitry are disposed.

Still yet even another embodiment of the present invention provides such a system wherein the biocompatible package is configured from a biocompatible material selected from the group of biocompatible materials consisting of ceramic, silicon, alumina, and liquid crystal polymer.

A still even yet further embodiment of the present invention provides such a system further having a conductive polymer bonding components of the sensor package.

Another embodiment of the present invention provides such a system wherein the pressure sensor is a micro-electromechanical system pressure sensor.

A further embodiment of the present invention provides such a system, wherein the pressure sensor is a capacitive sensor.

One embodiment of the present invention provides a system for the transmission of power through living tissue, the system having; an implanted radio frequency transceiver disposed within an implant unit, the implant unit being configured to be disposed within a subject's body and beneath living tissue; an external radio frequency transceiver coupled to a power supply; the external radio frequency transceiver being configured to transmit radio waves through the living tissue to the implanted radio transceiver whereby the radio waves are converted to electrical energy.

Another embodiment of the present invention provides such a system wherein the internal radio frequency transceiver being configured to transmit data from the implant unit to the external radio transceiver.

One embodiment of the present invention provides a system for the transmission of data from a biomedical implant, the system comprising: an an inverted-F antenna; a low temperature co-fired ceramic substrate upon which the antenna is disposed; an integrated means of wireless power transfer; and the antenna is configured with single layer shorting pins and from high-K material disposed about the perimeter of the implantable device in a single loop.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
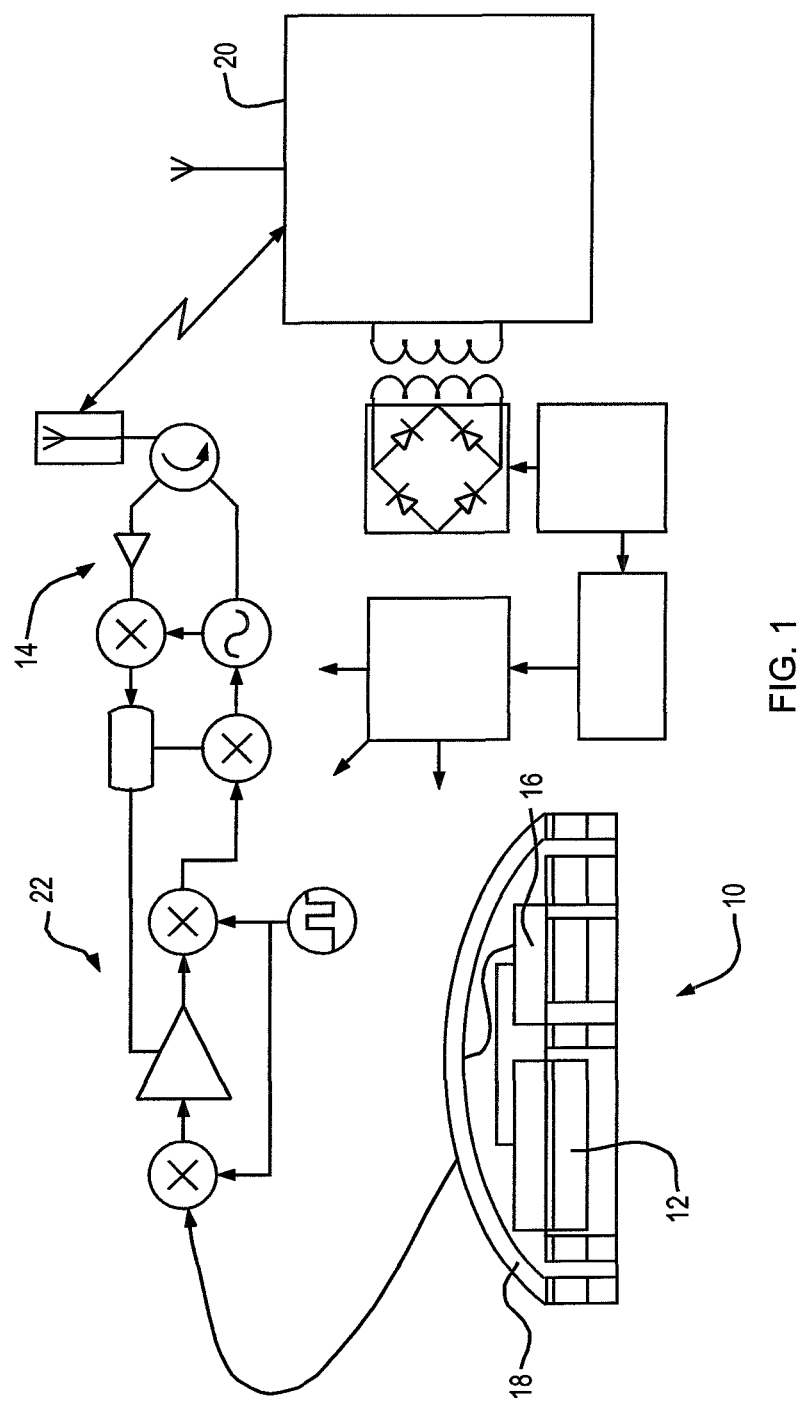
FIG. 1 is a block diagram illustrating a wireless Intra ocular pressure sensor configured in accordance with one embodiment of the present invention.
Figure 2:
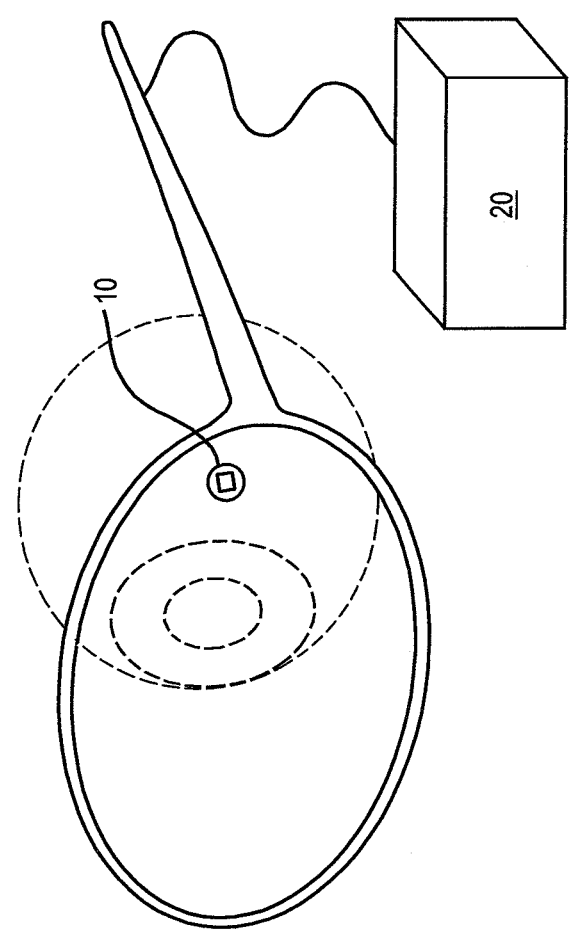
FIG. 2 is a schematic diagram illustrating a wireless Intra ocular pressure sensor configured in accordance with one embodiment of the present invention.
Figure 3:
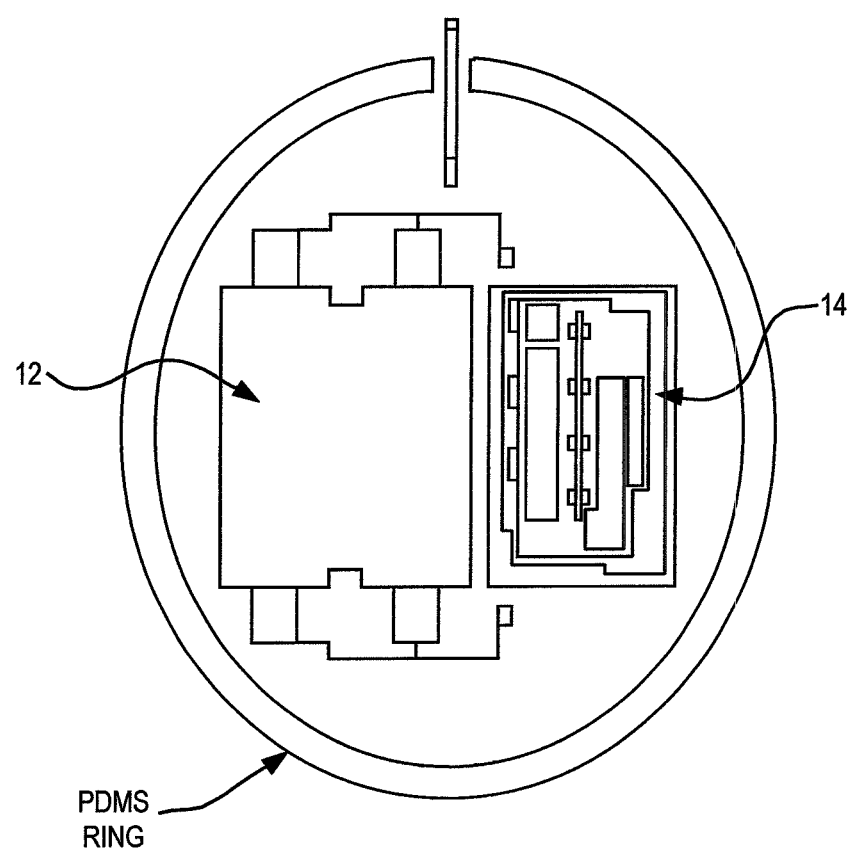
FIG. 3 is a micrograph illustrating a wireless Intra ocular pressure sensor configured in accordance with one embodiment of the present invention.

In one embodiment of the present invention, an intraocular pressure sensor implant package 10 is provided having a piezoresistive or capacitive pressure sensor 12, a wireless transceiver 14, integrated circuit 16, and, in one embodiment of the present invention, a silicon rubber ring 18. In some embodiments, the silicon rubber ring is omitted. Such an embodiment is illustrated in FIG. 1. An external transceiver 20 is also supplied to receive data from the sensor unit 12. The external transceiver 20 may be disposed in an external unit coupled to eye-glass or spectacle frames of the user, or may periodically be brought into proximity with the eye of the user to facilitate download of stored data. An embodiment where the antenna of the external transceiver 20 is disposed in spectacles is illustrated in FIG. 2.

One embodiment of the present invention provides a device for wireless sensing of the continuous measurement of intraocular pressure (IOP). Elevated IOP, which may result in the development of glaucoma, can damage the optic nerve that carries visual information from the retina to the primary visual cortex. If untreated, glaucoma can lead to irreversible blindness. Knowing that glaucoma is the leading cause of irreversible blindness in the world, the value of detecting increased pressure levels cannot be overstated. Since IOP can vary over the course of hours, not the months or weeks that transpire between office visits, patients may be misdiagnosed with false-negatives which reduce the chance of timely medical intervention. Additionally, patients may experience vision-endangering increases in IOP prior to the next office visit, without the opportunity for proper treatment. Thus, continuous-time monitoring is desirable.

In one embodiment of the present invention, the package may be configured to mate with, or be disposed in contact with a shunt disposed in the suprachoroidal space. Additionally, the sensor package may contain channels for the shunting of aqueous humor, thereby acting as a glaucoma drainage device. Alternatively, the sensor package 10 may be disposed in the suprachoroidal space, and effectively measure the pressure of the outflow of the aqueous humor from the anterior chamber. One skilled in the medical device arts will appreciate that pressures of such a nature would be valuable in other areas of the body, and that with suitable adaptation of the package. Examples of such modifications include to the shape of the package, allowing placement in the pulmonary arties for measurement of systolic blood pressure, or other pressure sensitive measurements required by the clinician.

In one embodiment of the present invention, the package may be configured in the shape of a ring, which would mate with a suprachoroidal shunt and form a drainage reservoir. Alternatively, the package may assume other forms that would provide structural or functional support to the implanted shunt. In an alternative embodiment of the inductively-powered IOP sensor device, the output signal from the IOP sensor 12 may be employed to actuate an active shunt valve or flow restriction, which would allow for a fully-active IOP sensor and shunt system. In one embodiment of the present invention, the device may be configured in a roughly rectangular shape that is bent to conform to the curvature of the patient's eye.

Packaging of the device may in one embodiment be a streamlined enclosure of ovular or circular top view. The package may be manufactured from a biocompatible polymer, ceramic, or metal, or other suitable material. One side of the package is provided with a membrane permitting the pressure of the aqueous humor to be in contact with the sensor 12 while maintaining the integrity of the package. The packaging of one embodiment must be of a size and shape configured to be received into the suprachoroidal space of the eye.

The silicon rubber ring of one embodiment of the present invention absorbs package stress and reduces long term drift of the device. In other embodiments the ring may be omitted as necessitated by the structure of the sensor and the ceramic package in which it is disposed.

The integrated circuit 16 is in one embodiment bonded to a durable substrate which contains pad layouts for the chip and external components, interconnects, and an antenna. Low-Temperature Co-fired Cermaic (LTCC) is a suitable option for assembling this complete system due to its multilayer and integration capabilities. Specifically of interest is the capability to have small scale cavities and hermetic bonding. Furthermore, this ceramic can provide sufficient structural integrity with very thin layers. LTCC also provides a high dielectric allowing for miniaturization of the antenna. Dupont 951 was chosen as a demonstrator because of the relative ease of processing and availability, one skilled in the art will appreciate that other materials may also be used. This proof of concept is a vehicle for showing the suitability of a variety of LTCC tape substrates which are under consideration for the final implantable system. Biocompatibility tests of a variety of tape systems are currently in progress. The size and form factor achieved with this demonstrator is representative of any of the other LTCC materials.

Figure 4:
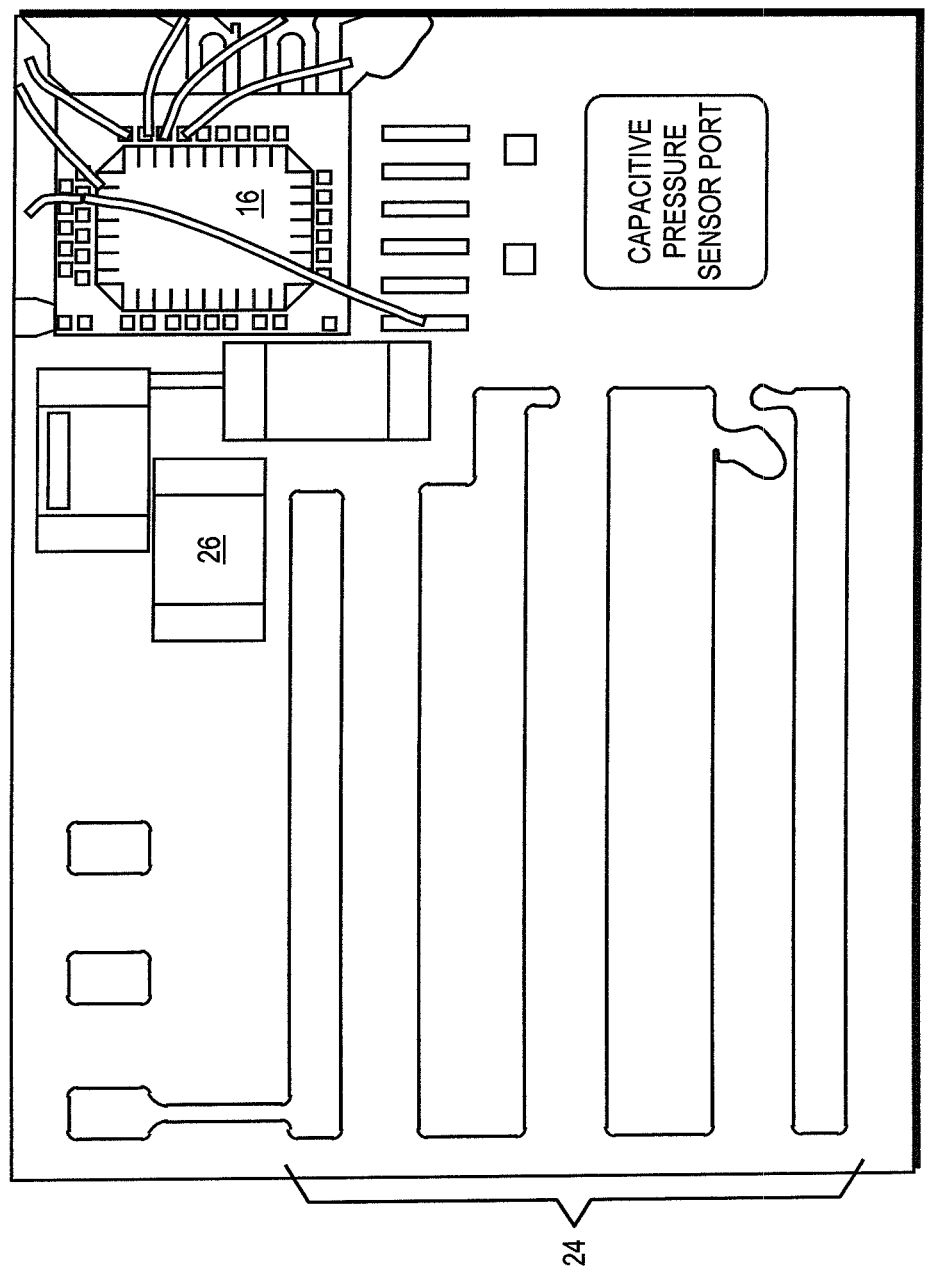
FIG. 4 is a micrograph illustrating a wireless transmitter LTCC circuit board configured in accordance with one embodiment of the present invention.

In addition to the integrated circuit 16 and antenna, the final device also contains a capacitor array 24 for internal power storage and a pressure sensor. Cadence software is used to draw the layout of the pads, interconnects, and antenna. The LTCC board used for the initial study contains all the traces for the final device and the cavity for the sensor but is only populated with the components necessary for wireless telemetry. The LTCC board is fabricated through standard processing of the tape layers, screening traces, creating vias, laminating layers together, and finally firing. Then, matching network components 26 for the antenna 28 are soldered on, and external wires for supplying power and digital data are attached using conductive epoxy. Lastly, the transmitter ASIC 16 is attached to the substrate and wirebonded. The assembled transmitter LTCC board is shown in FIG. 4. The size of the final device is only a few millimeters on either side.

In an alternative embodiment, silicon, was used to implement different antenna prototypes and to test alternative low-profile bonding methods. Silicon has several advantages including the fact that it is known to be biocompatible. Furthermore, photolithography techniques allow us to achieve small scale interconnect traces and footprints for minimal area bonding techniques, reducing the overall size of the device. For this approach, we start off with a silicon wafer with high resistivity ($\rho$=10,000 $\Omega \cdot$cm) and use an E-beam evaporator to deposit a 50 nm layer of Ti and a 0.7 $\mu$m layer of Au. The pads on the silicon board, to be connected to the integrated circuit pads, are created using a photo-resist and etching lithography process.

Figure 5:
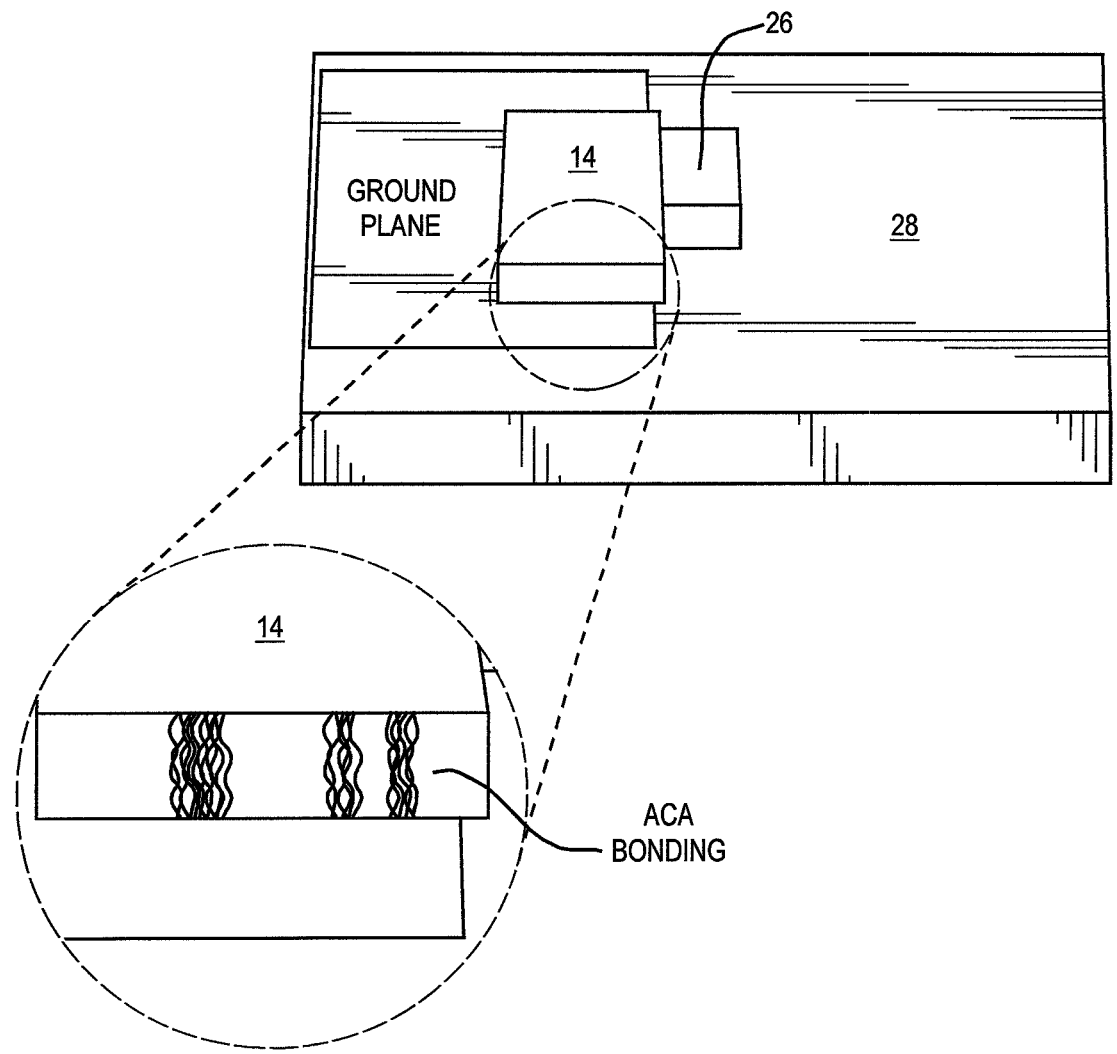
FIG. 5 is a micrograph illustrating a Silicon transmitter board with anisotropic conductive adhesive (ACA) bonded IC configured in accordance with one embodiment of the present invention.

For the connections between the pads on the silicon board and those on the integrated circuit, 16, shown in FIG. 5, we use a novel magnetically aligned z-axis anisotropic conductive adhesive bonding process developed by Nexaura Inc. Such an adhesive requires only a thin-bonding layer (on the order of tens of $\mu$m), is lead free, allows for direct bonding without patterning, and uses a low-temperature curing process. The use of silicon and lithography allows for implementation of this bonding process to produce a direct attachment of the integrated circuit 16 using a flipped approach. By comparison, the wirebonding method used for the LTCC board, increases overall device thickness and width to dimensions that may be too large for implant in the suprachoroidal space, and requires careful handling and packaging of the wires. The resolution of the screen-tracing on LTCC and the miniature size of the integrated circuit pads limited its attachment method to wirebonds or the aforementioned z-axis conductive adhesive bonding.

The z-axis anisotropic conductive adhesive consists of an epoxy material with suspended conductive particles. These particles are comprised of a Ni core coated by 8% of Au. When a static magnetic field is induced, the conductive particles with ferromagnetic material create vertical columns in the adhesive. The interaction between conductive columns makes their distribution uniformly spaced in the horizontal plane. These columns allow for current to flow in only the vertical direction. An analysis of the column distribution showed that the columns are on average approximately 10 $\mu$m in diameter.

A layer of anisotropic conductive adhesive is applied onto the silicon board over the desired location of the integrated circuit. 16. A flip-chip bonder with 5 $\mu$m accuracy is used for positioning, alignment, and placement of the integrated circuit 16 on the silicon board. The adhesive is cured for 15 minutes in the presence of a 0.25 tesla static magnetic field. Our integrated circuit, 16, with small 75×75 $\mu$m$^2$ pads with a 25 $\mu$m separation, was easily bonded with high reliability. The final layer of anisotropic conductive adhesive is measured to be about 50 $\mu$m thick. The rest of the assembly process consists of attaching lumped components using a conductive epoxy and coating the entire board with a thin layer of biocompatible Parylene or other suitable material.

The piezoresistive pressure sensor 12 is, in one embodiment disposed on a silicon-on-insulator wafer 22 with etched cavities 24 wherein the wireless transceiver 14 is disposed. In alternative embodiments, capacitive sensors may be utilized, decreasing package size and noise and increasing sensitivity of the sensor. A capacitive sensor may be proved configured according to one embodiment of the present invention.

An implantable power storage device may also be provided within the implantable device package 10. In some such embodiments, the power storage device can be recharged with an external, primary coil inductively coupled with an internal secondary coil disposed within the implant package. An AC current is induced, and converted to DC to charge the power storage device using efficient CMOS rectifiers and charge capacitors. In alternative embodiments, the implantable device may be powered entirely through conversion of localized biological sources of energy, such as a maintained temperature differential between surrounding tissues. In one embodiment, power may be supplied via RF transmission. This allows greater flexibility to the user regarding alignment of the recharging apparatus while allowing the use of a single antenna for both transmission of data and power.

A transmitter ASIC 16 (application-specific integrated circuit) design is provided, according to one embodiment of the present invention, achieving high power efficiency by minimizing power consumption while maximizing power output. Other design specifications include achieving a resonant frequency around 2.4 GHz, a frequency bandwidth of at least 1 MHz, and an output match to drive a 50Ω antenna. The main components of the transmission portion of the ASIC are a voltage-controlled oscillator (VCO) and a power amplifier 22. The input data to be transmitted comes from internal digital memory storing 24 hours of measurements in serial form. The binary frequency-shift-keying (BFSK) digital modulation scheme is chosen to provide some immunity to tissue induced attenuation noise while maintaining a relatively simple and low power design.

Figure 6:
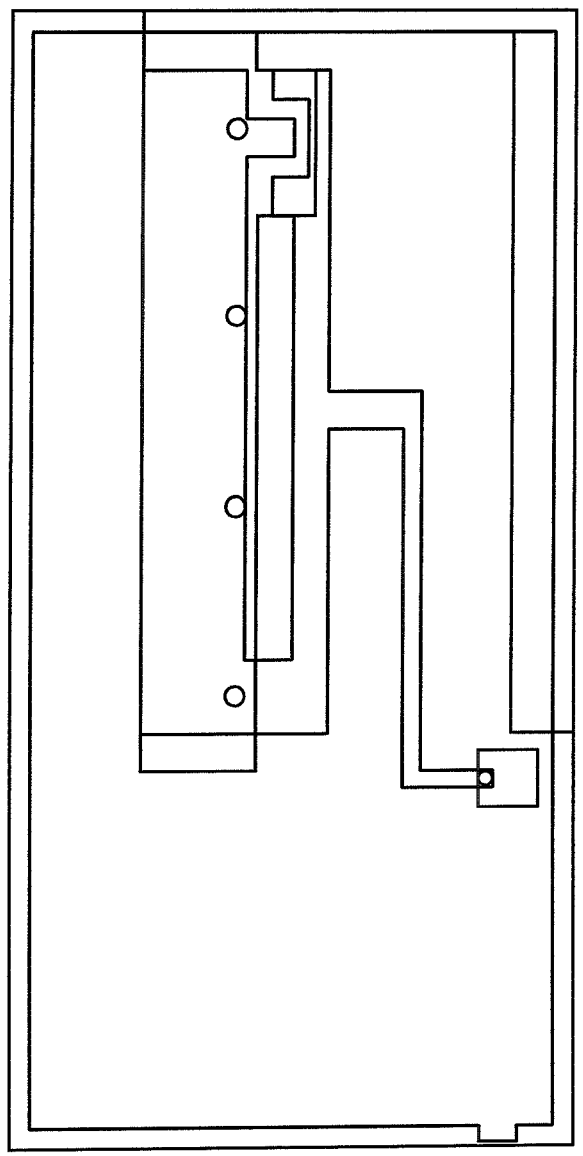
FIG. 6 is a planar view illustrating an embedded antenna structure configured in accordance with one embodiment of the present invention.

A direct input-voltage to frequency conversion using a VCO accomplishes the frequency modulation in a system configured according to one embodiment of the present invention. For such a VCO design, the NMOS cross-coupled pair topology, is used shown in FIG. 6, due to its advantages in a low voltage application. A major component in the cross-coupled VCO is the variable capacitor (varactor), used to vary the frequency of oscillation. The varactor is placed in parallel with the tank capacitance and its variation with input-voltage produces the oscillator's tuning curve. To achieve a monotonic variation of capacitance, it is necessary to keep the MOS capacitor in one region of operation. Inversion region is selected by biasing the bulk potential to Vdd, which maintains this region of operation for all input voltages.

In an effort to maintain a high level of integration, which leads to a smaller overall intra-ocular pressure sensor design, on-chip reactive components are desirable, a monolithic microwave integrated circuit (MMIC) is used. The NMOS cross-coupled VCO requires two inductors, which are designed to produce the desired oscillation frequency, obtain the desired tank amplitude, ensure startup for our projected bias current, and achieve minimal phase noise. For the design of our inductors a model for phase noise obtained through evaluation of its time variant phase impulse response.

For the layout of the inductors configured according to one embodiment of the present invention, octagonal spirals are used, increasing the quality factor (Q) by 10% over square inductors. Increasing the number of turns increases inductance but if the turns are added to the inside of the coil, the increase in inductance decreases with smaller radii as they add a decreasing amount of magnetic flux while contributing significantly to the eddy current loss resistance. Conversely, adding turns to the outside of the coil increases overall size. A 3-to-1 ratio between outer diameter and inner diameter gives a reasonably optimal design for Q, inductance, and size. The layout of such an inductor uses the topmost metal layer which has the greatest thickness and therefore lowest series resistance, and is furthest from the substrate which reduces parasitic capacitances.

The final VCO topology works as an inductor-capacitor (LC) tank circuit. The variation of capacitance with input-voltage to the varactors, changes the tank resonant frequency variation and frequency modulates the digital input.

The monitoring system configured according to one embodiment of the present invention takes pressure measurements at regular intervals throughout a 24-hour period. Internal power storage 24 is required to provide the direct current (DC) power for driving the circuits. Every 24 hours, the power storage unit can be recharged by coupling from an external RF source and rectifying the signal to a DC current. The power conversion efficiency (PCE) depends on the biasing of the rectifier circuit and determines the operating range and charging time. Although a charge pump can be used to amplify the voltage, the raw voltage out of the rectifier is presented in this paper, since ideally a charge pump will not be required. In this way the embodiments of the present invention can provide a fully integrated system which includes the powering circuitry, power storage unit, bio-sensor, transceiver, μ-processor, and embedded antenna.

Figure 8A:
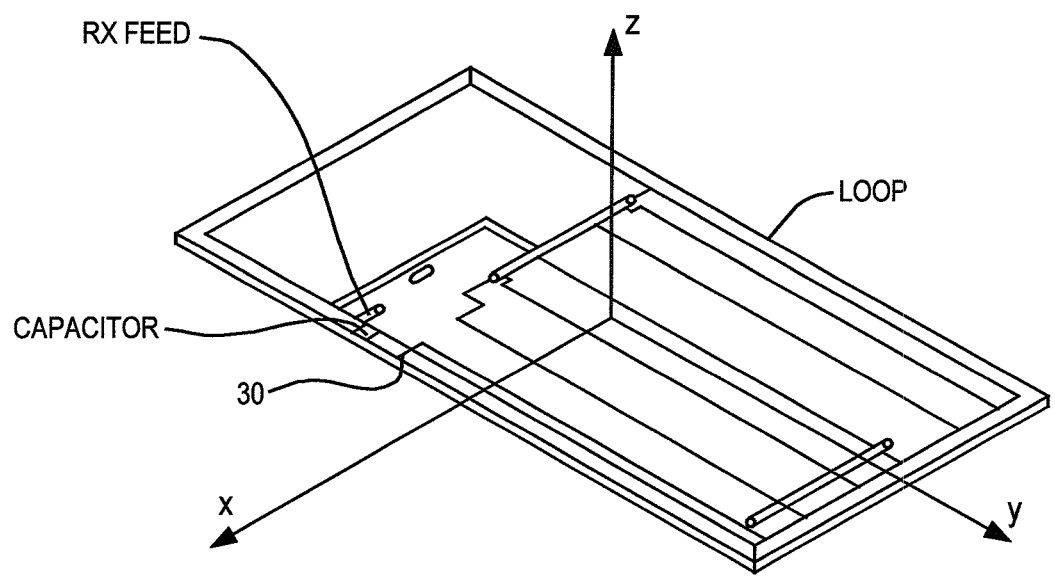
FIG. 8A is a perspective view illustrating a loop antenna embedded between LTCC layers configured according to one embodiment of the present invention.

The implementation of embedded antennas 28 face major challenges posed by the maximum length constraint of less than 4% of the wavelength, the proximity of a truncated ground plane, the nearby metal pads and interconnect wires, and the limited quality factor of matching networks at these sizes. An inverted-F-like feed is designed on a single layer LTCC (Dupont 951), as illustrated in FIG. 8A which has a high dielectric constant of 7.8. To maximize the use of the limited substrate, the perimeter is surrounded by a single loop antenna which is fed by the inverted-F like structure via coupling. An additional capacitive load is attached to the end of the feeding structure to increase efficiency. The complete structure is shown in FIGS. 6A and 6B.

The area allowed for the antenna in one embodiment of the present invention has a maximum length of 6 mm (<5% of the 2.4 GHz wavelength), drastically reducing the efficiency. Furthermore, the thickness requirement of the board only allows for minimal spacing between the antenna and metal traces, pads, and ground plane 30, increasing the parasitic coupling.

LTCC was chosen in one embodiment of the present invention, for its ease of fabrication, durability, high dielectric, and multilayer capabilities. A resulting design is illustrated in FIG. 8A where the outside loop surrounds the perimeter of the substrate, maximizing our usage of the limited area available and promoting magnetic field storage. To help compensate for the miniature size of the loop, a finely tuned capacitor can be used across the antenna terminals to improve the efficiency. In an effort to maintain a complete and unbroken loop, the capacitor is placed at the end of the loop. There are notable advantages in this design including: ease of fabrication in LTCC as an embedded antenna combined with matching circuitry, and the ability to transfer data and couple power using the same structure.

Figure 8B:
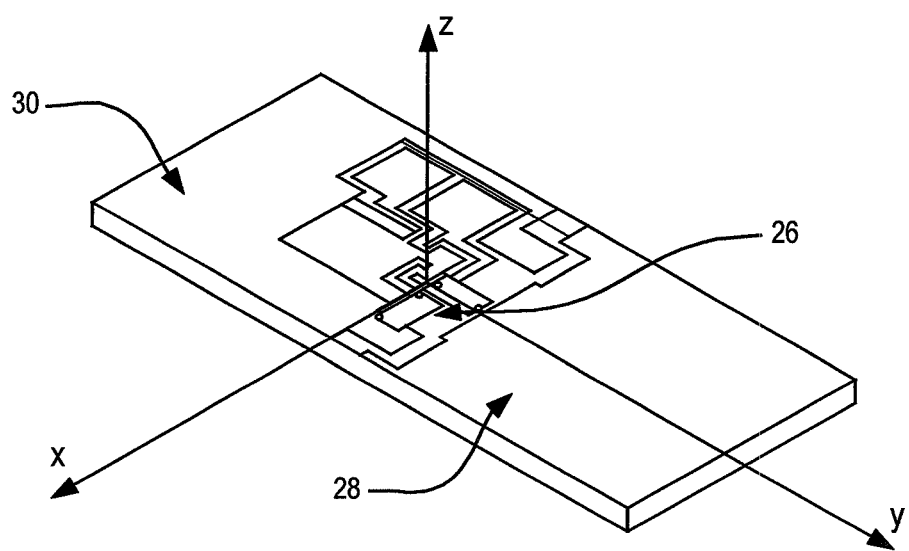
FIG. 8B is a perspective view illustrating a monopole antenna on silicon substrate configured according to one embodiment of the present invention.

In an alternative embodiment, silicon-on-silicon packaging may be used for its smaller allowable feature sizes, known biocompatibility, and mature fabrication process. Size specifications of one such embodiment constrain the maximum length and limit the efficiency. A monopole antenna, shown in FIG. 8B, is an efficient and robust structure after assembly.

This design maximizes the use of the limited area, allows for fabrication into LTCC as an embedded antenna, and induces a magnetic propagating wave which faces little attenuation through body tissues. Low efficiency may be tolerated considering the minimal size of the device, and since this application requires only a range of meters, the efficiency value obtained is acceptable.

One skilled in the art can appreciate that there are different types of circuits which convert RF power into DC power such as a single diode peak detector, a bridge rectifier, a charge pump rectifier, and a multiple-stage Schottky diode voltage multiplier. The design concerns of the power circuitry include power conversion efficiency, input power, power consumption, size, and integration. To minimize power consumption, a voltage multiplier is provided due to its low input power requirement. The output voltage of the multiplier is directly proportional to the number of stages, N. Therefore, a large output voltage can be achieved by increasing the number of stages and available RF power into the circuit, as well as by lowering the diode threshold voltage.

Figure 9:
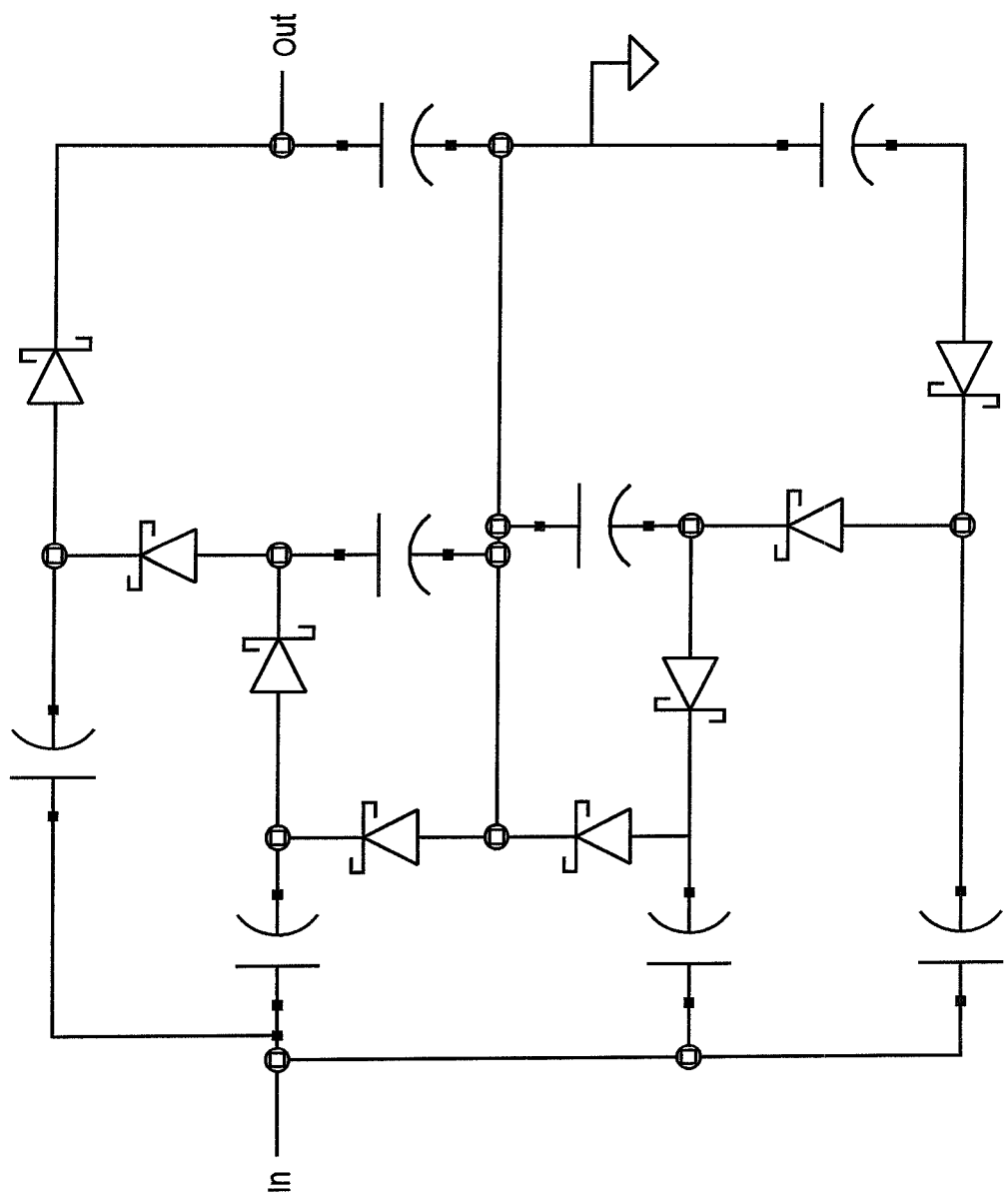
FIG. 9 is a schematic diagram illustrating a 2-stage voltage multiplier in ADS simulation configured in accordance with one embodiment of the present invention.

Schottky diodes are used in one embodiment of the present invention because of their low forward-biased voltage drop ($V_F$), fast reverse-recovery time ($t_{rr}$), and low junction capacitance ($C_J$). A voltage multiplier circuit schematic is shown in FIG. 9. In one embodiment of the present invention, the voltages across the capacitors in the odd and even stages are charged in an alternating fashion between positive and negative phases to accumulate multiples of the input voltages. In this type of circuit the currents through the capacitors are large relative to that drawn by the load. This implies in particular that as the stages increase, the voltage increases marginally due to the parasitic resistors and leakages. Output voltage is determined by multiple factors including $R_{load}$, $I_{bias}$ (input power), capacitor values, and operation frequency.

Figure 10A:
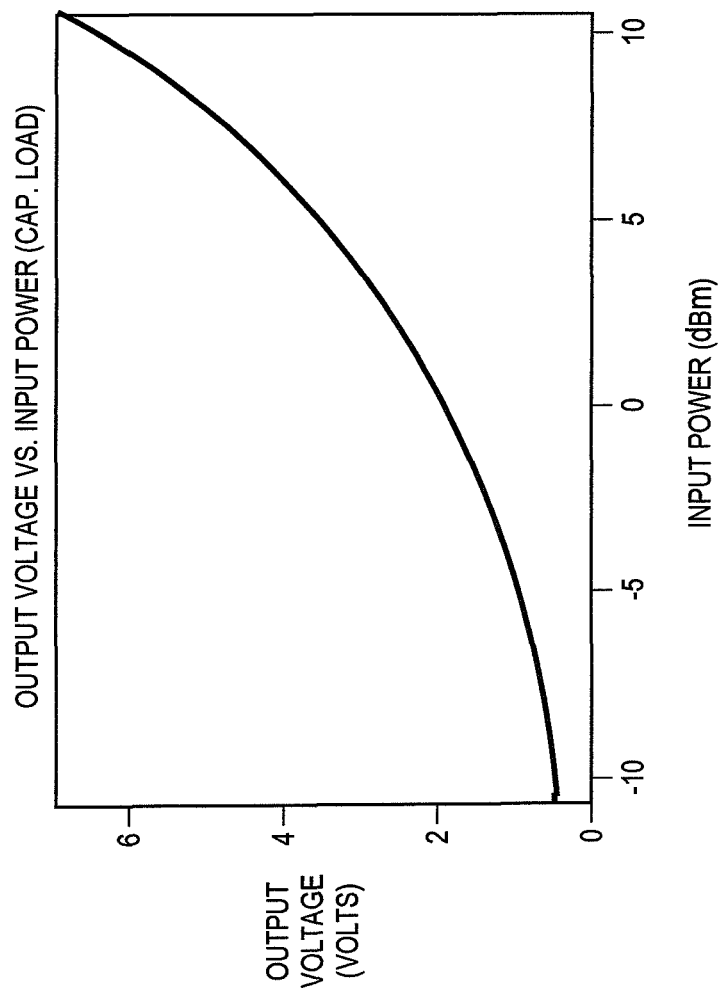
FIG. 10A is a graph illustrating Simulation results of design parameters: Vo (volt) vs. (a) PIN (dBm) of a wireless Intra ocular pressure sensor configured in accordance with one embodiment of the present invention.
Figure 10B:
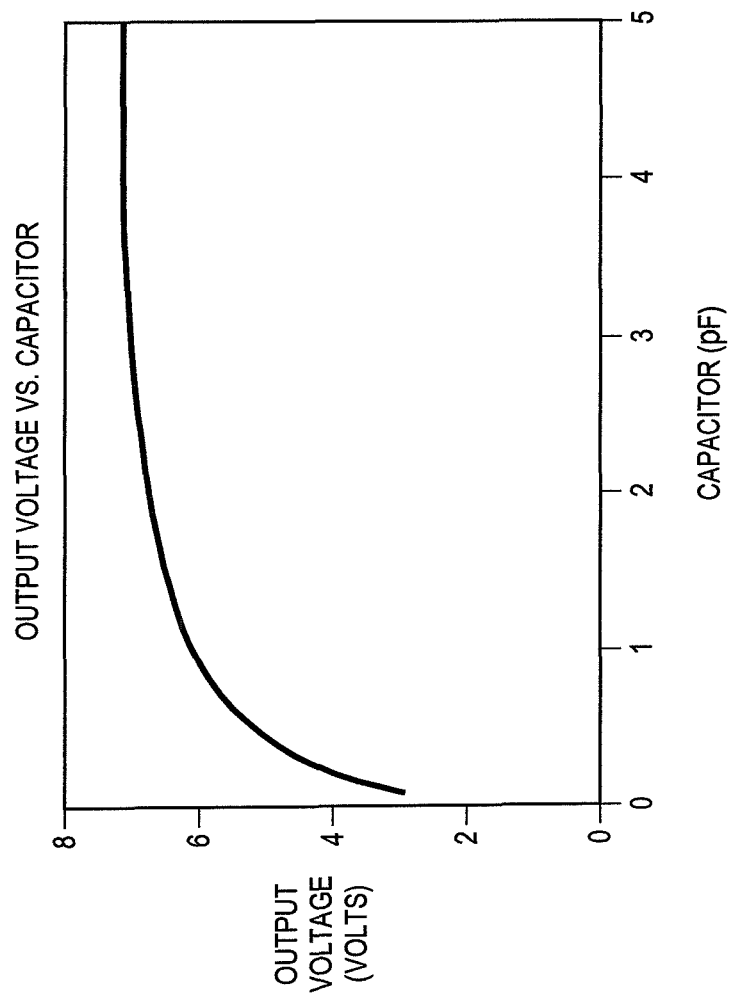
FIG. 10B is a graph illustrating Simulation results of design parameters: Capacitor values (pF) of a wireless Intra ocular pressure sensor configured in accordance with one embodiment of the present invention.
Figure 10C:
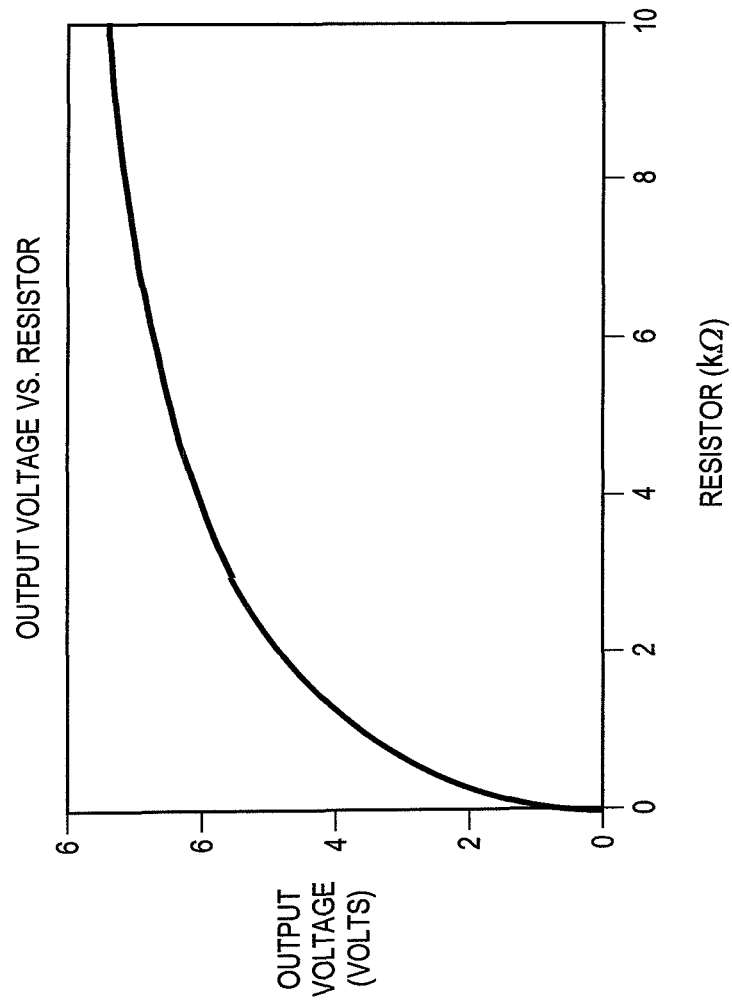
FIG. 10C is a ph illustrating a wireless Intra ocular pressure sensor configured in accordance with one embodiment of the present invention.
Figure 11:
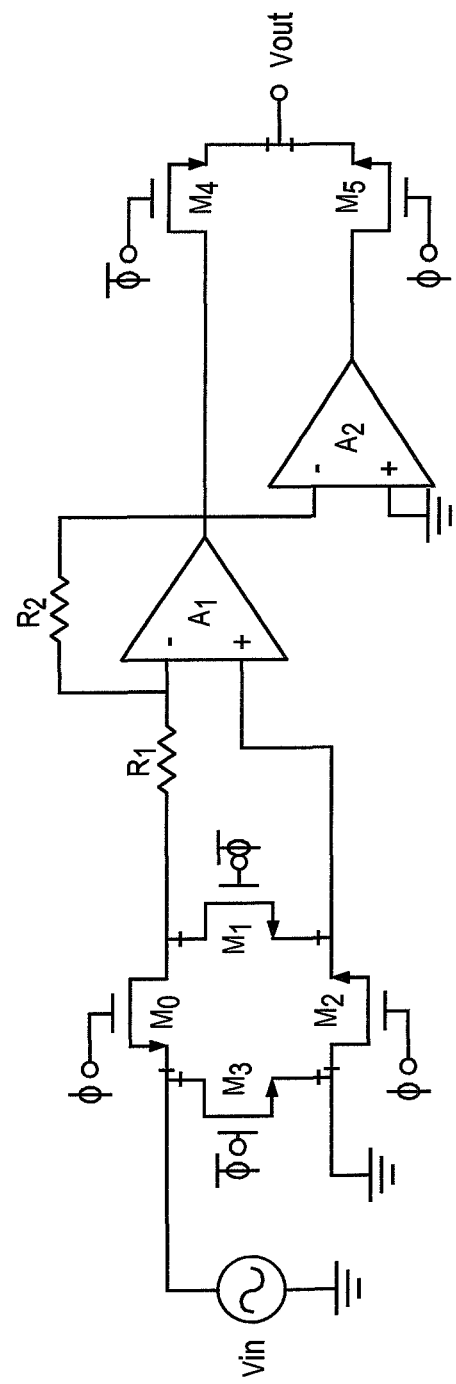
FIG. 11 is a block diagram illustrating a sensor circuit configured in accordance with one embodiment of the present invention.

Design choices include the values of capacitance in the voltage multiplier ladder and the load capacitor which is used to store the rectified current. In these examples, a 10 µF capacitor is used as a representative load. FIG. 10A shows the output power versus input power, FIG. 10B shows the output voltage as a function of the circuit capacitors, and FIG. 10C demonstrates the ability to drive the rectified current into a real load in parallel with the storage capacitor. This would represent the load presented to the bias of an IC when it is operational. Of note, is that the performance of the simple capacitor is reached if the load is greater than 8 KΩ. Voltages of 4.8 V were created across the 10 KΩ load.

In one embodiment a Biological Micro Electro Mechanical System (BioMEMS) based pressure sensor and appropriate recording electronics can be inserted through the sclera and placed in contact with the choroid. This method of measuring IOP in vivo is feasible. The inductively-powered, implanted unit will wirelessly transmit IOP measurements to an external data-logging device, where the continuous-time data can be observed, analyzed, saved for future analysis, or transmitted via the internet to a centralized clinical data management system. In the event that predetermined thresholds are exceeded, data can be sent on directly to the primary care or other physician via the external device between office visits, the primary care physician or disease-specialist would be able to monitor the patient remotely via the data management system user-interface.

Alternatively, in one embodiment, an externally disposed charging transceiver base that allows for daily downloading of data and charging of the device may be employed. In such an alternative embodiment, data may be stored on the implantable device until downloaded to the external device at a convenient time to facilitate greater freedom of movement by the patient or otherwise decrease the need for constant external devices. An inductively-powered, implanted unit may transmit and receive data according to the accepted IEEE 802 or Bluetooth protocols, and may utilize this communication protocol to transmit IOP spikes or other dangerous symptoms to the appropriate medical professional. An RF powered device may use suitable RF protocols for the transmission of data while permitting the recharging of the device through a RF antenna rather than via an inductive coil, saving both space and providing increased range.

Figure 12:
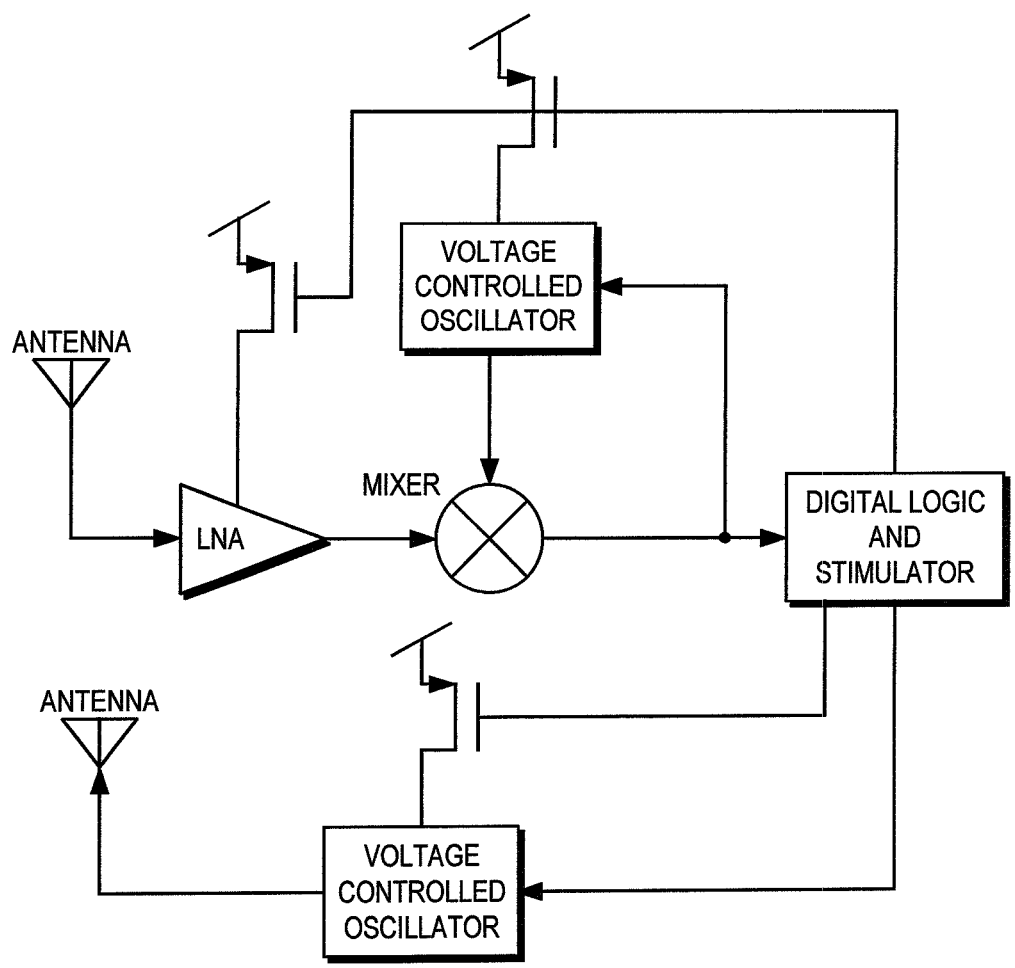
FIG. 12 is a block diagram illustrating a telemetry circuit configured in accordance with one embodiment of the present invention.

Data collected by the sensor and data communicated to the sensor by the external transceiver is transmitted by means of a radio frequency (RF) carrier wave, whereby it is propagated wirelessly through the biological tissues. In one embodiment digital modulation may be used with such a signal, while various modulations schemes, both analog and digital are well know to those skilled in the art. In one embodiment frequency shift keying is employed to minimize noise and preserve data integrity for the effects of a fading RF signal. A design such as that illustrated in FIG. 12 may be utilized for a reliable high frequency device.

Due to the inherently low-voltage of inductive powering or RF powering schemes, ultra-low-power circuits are desirable. Furthermore, compact circuit size is desired for implantable electronics. In an effort to meet these needs, an ultra-low-power, fully-implantable, wireless system for continuous, long-term IOP monitoring was developed. A compact, nanopower, CMOS operational amplifier that can be incorporated into a wireless IOP monitoring system was designed and fabricated. The amplifier has an optional low output impedance buffer that can be utilized for driving low-impedance loads.

Figure 13:
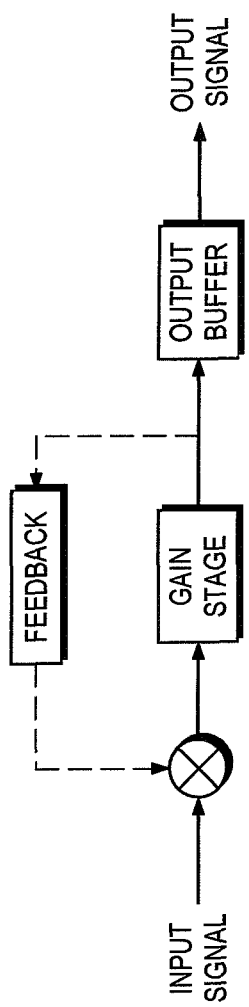
FIG. 13 is an operational amplifier block diagram with off-chip feedback network.

The operational amplifier of one embodiment of the present invention consists of two major building blocks, a gain stage and an optional output buffer, as illustrated in FIG. 13. An off-chip negative feedback network around the gain stage can be added to provide gain desensitization and improve linearity. The low output impedance buffer can be utilized should the amplifier be required to drive a low-impedance load.

All the circuits presented operate in the subthreshold region where the drain current can be approximated as:

$$I_D = \frac{W}{L} I_{D0} e^{\left(\frac{V_{GS}}{n(kT/q)}\right)}.$$

This exponential dependence of $I_D$ on $V_{GS}$ occurs for:

$$V_{GS} < V_T + n\frac{kT}{q}.$$

Operation in the subthreshold region allows for substantially lower device currents compared to the moderate and strong inversion regions, thus leading to lower power circuits. In addition to subthreshold operation, the circuits are designed with a minimal number of components to provide minimal chip area. Device lengths greater than the minimum process length are used to improve channel length modulation effects.

Figure 7:
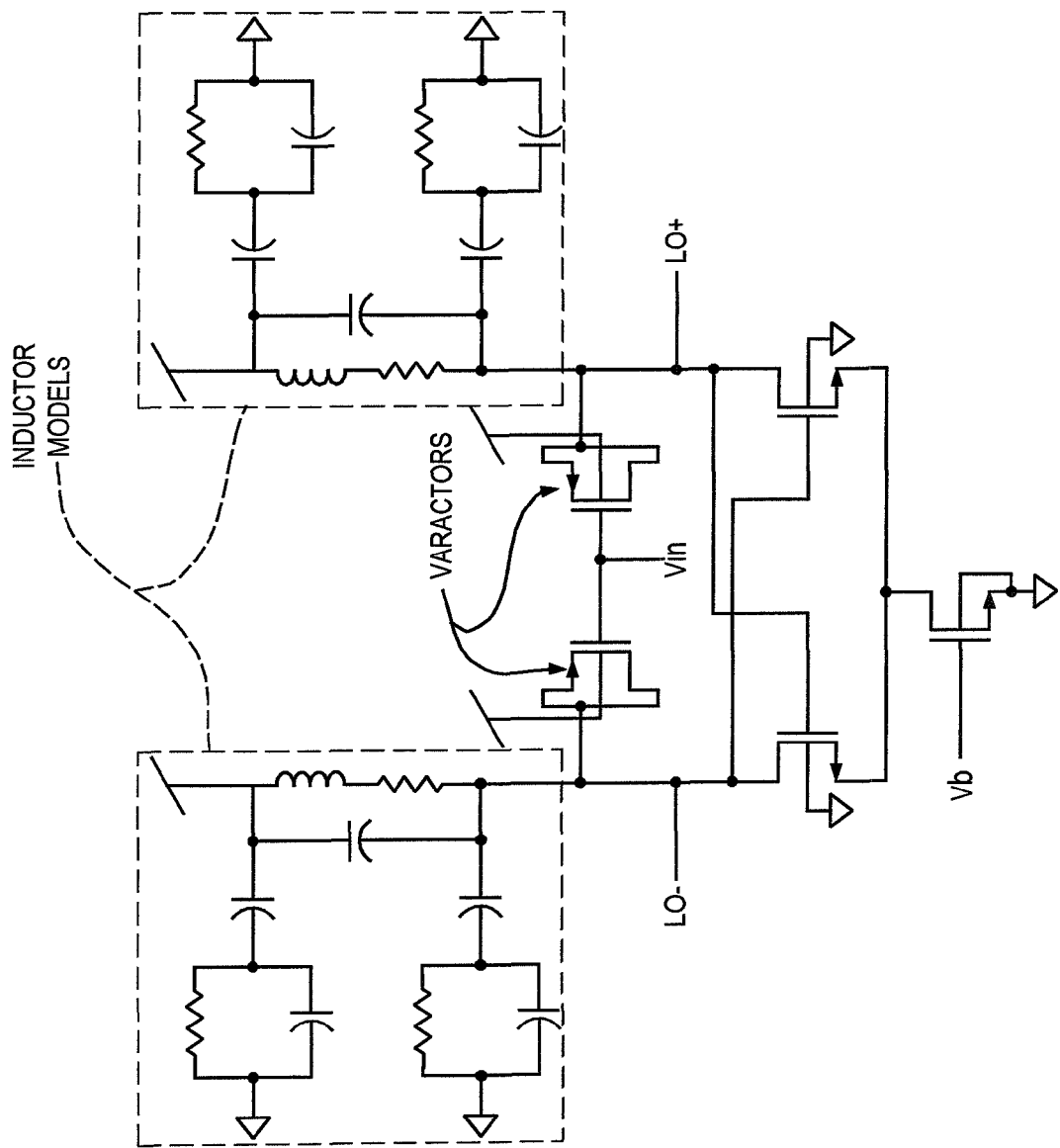
FIG. 7 is a diagram illustrating a wireless NMOS cross-couple pair VCO with PMOS varactors and inductor models configured in accordance with one embodiment of the present invention.

The gain stage in FIG. 7 consists of a current-mirror based input differential amplifier and a single-ended common-source (C-S) output forming a two stage architecture. A PMOS input transistor pair ($M_1$, $M_2$) can be utilized to decrease 1/f noise. Furthermore, the area of these transistors can be made large to further reduce 1/f noise. The body of each input transistor can be connected to the respective sources to eliminate threshold voltage variations associated with input common-mode voltage deviations. The W/L ratios of current-mirror transistors ($M_3$, $M_4$) can be made close to unity to provide proper biasing of the C-S input transistor, $M_6$. Miller frequency compensation can be implemented through $R_1$ and $C_1$ placed between the gate and drain of $M_6$.

Figure 15:
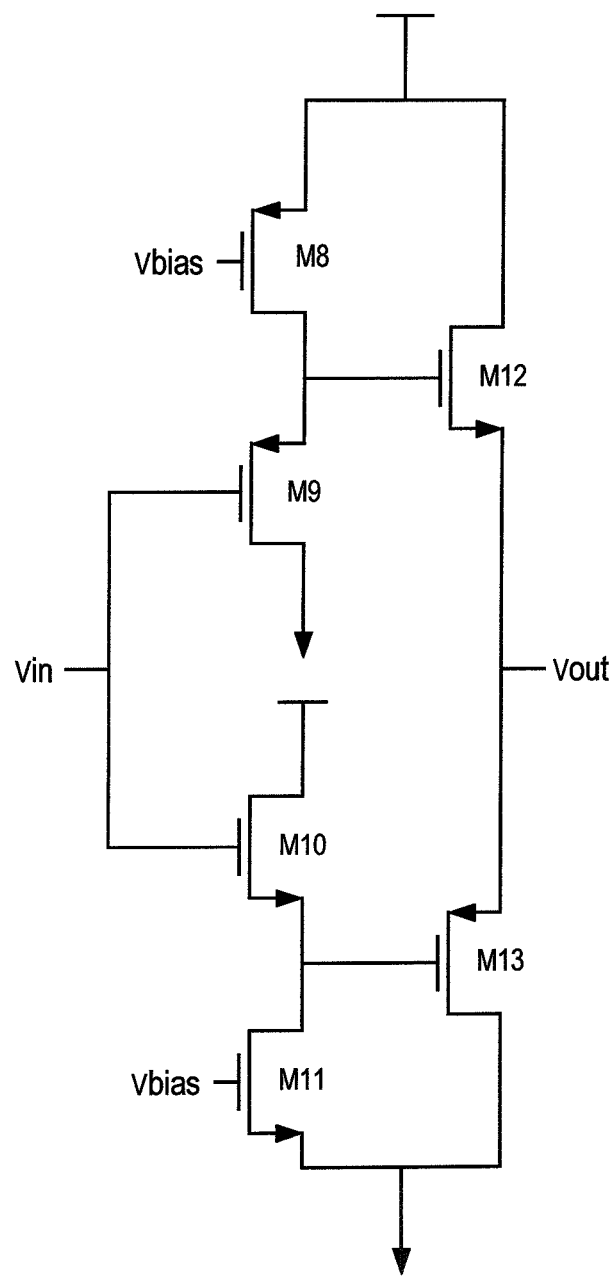
FIG. 15 is a subthreshold class AB output buffer circuit implementation for low output impedance.

The minimum output impedance of the gain stage can be approximated as:

$$r_{out} = \frac{r_o}{2},$$

when $r_o = r_{o6} = r_{o7}$. Even at a minimum, the output impedance can be 100 kΩ or greater. Because of this, impedance matching to low-impedances can be difficult to achieve. Such matching may be necessary if the amplifier is to drive a low-impedance load. To obtain low-impedance matching, the push-pull source follower of FIG. 15 can be used. The complementary source followers formed by transistors $M_8$-$M_{11}$ sufficiently bias the output transistors ($M_{12}$, $M_{13}$) into the deep triode region, thus essentially forming a voltage divider at the output. Since the small-signal output impedance of the buffer can be approximated as:

$$r_{out} = \frac{1}{g_{m12} + g_{m13}},$$

a low output impedance can be achieved by designing the W/L ratios of the output transistors appropriately.

Figure 16:
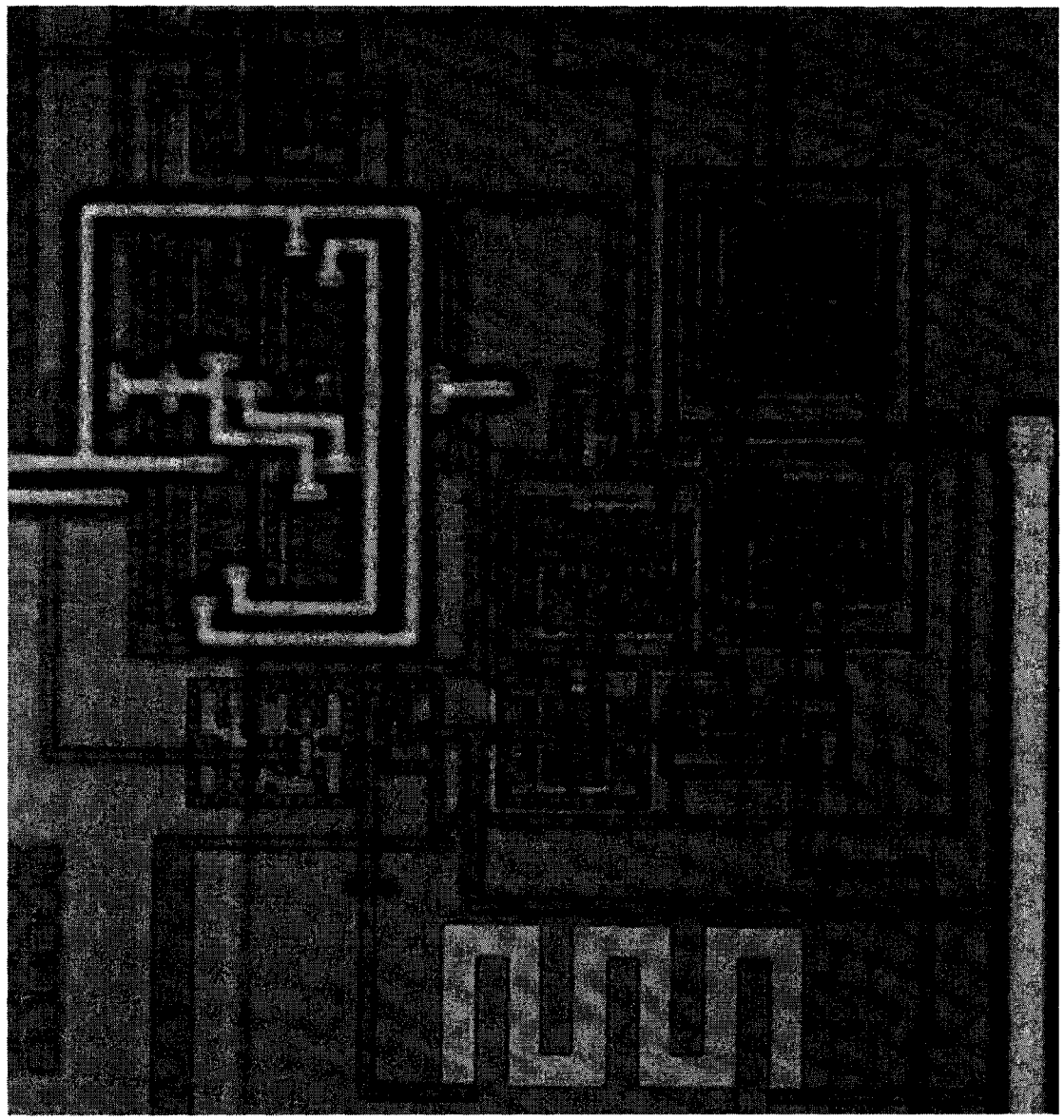
FIG. 16 is an IC micrograph of the fabricated ultra-low-power operational amplifier.

The circuits of one embodiment of the present invention described have been fabricated in the AMI C5 process characterized by minimum channel lengths of 0.6 μm. A micrograph of the fabricated operational amplifier is shown in FIG. 16. Layout techniques such as common-centroiding and multi-fingering were utilized.

The following provides a summary of representative circuit operational performance values. Data are typical values and were obtained while utilizing the optional low-impedance output buffer.

Figure 14:
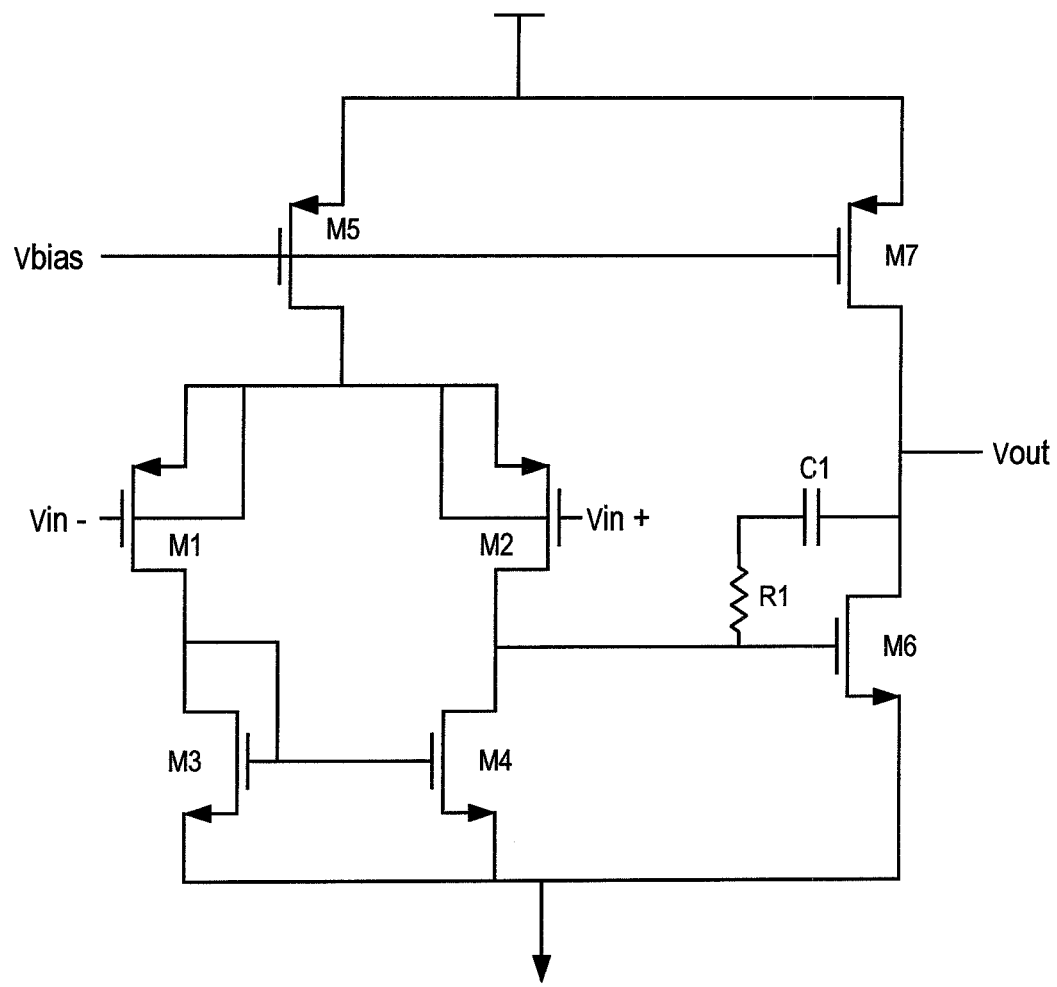
FIG. 14 is a subthreshold gain stage circuit implementation with differential amplifier input, common source output, and Miller frequency compensation.

During design of one embodiment of the amplifier several trade-offs were made to satisfy three main goals: ultra-low-power, compact layout area, and an amplifier having low output impedance. These tradeoffs are reflected in decreased values of open-loop gain, bandwidth, noise, and other parameters listed in FIG. 14. Despite these tradeoffs, the amplifier, of one embodiment of the present invention, will provide reliable results in certain applications including but not limited to IOP recording. Of these trade-offs, the easiest to observe is the low bandwidth of 9 Hz. Low bandwidth is typical of low-power systems as the two are intimately related. However, this is not a concern for the measurement of IOP as the fundamental frequency of the pressure signal is related to an individual's heart rate which can be approximated as 1-2 Hz.

The signal from the Voltage Controlled oscillator may be fed through a power amplifier to drive the transmit antenna. Class C power-amplifier topology was used in one embodiment of the present invention to achieve a good balance between power efficiency, chip area, and cost. The primary common-source NMOS transistor acts as a switch that controls the current supplied to the LC tank. Every time the transistor is on, a pulse of current keeps the tank pumped. The power amplifier is designed so that the transistor drives current when the output voltage is low and vice versa, minimizing the power consumption. To optimize the circuit, the on-resistance of the transistor is decreased by decreasing the length. Furthermore, to increase the efficiency of the amplifier, the on-time of the transistor is reduced while ensuring the on-time is still long enough so that the tank is charged up at every cycle. Increasing the transistor width allows the decrease of the required on-time while maintaining the power amplifier gain. Unfortunately, as this width is increased, the capacitance at the gate will increase and make it harder for the prior stage VCO to drive the power amplifier. The primary tradeoff is between efficiency and power output and thus we have to sacrifice some efficiency to ensure sufficient gain. To facilitate the design, we use the same inductor for the power amplifier's LC tank as for the VCO, and then use a parallel capacitor to achieve resonance at our operating frequency. The power amplifier is also fabricated as a MMIC with on-chip reactive components.

Provided that trade-offs such as low bandwidth and gain can be made, the operational amplifier of one embodiment of the present invention can be used for other biomedical/non-biomedical applications requiring ultra-low-power and compact size. For example, implantable cardiac monitors, wearable pulse oximeters, and implantable blood and brain pressure and electrical activity monitors could find use for the operational amplifier presented.

Low-power and minimal sized implantable electronics are desired for wireless sensing of IOP due to inherent issues associated with inductive power supplies and implantation area, respectively. The designed and fabricated CMOS operational amplifier could be used within such systems as it consumes only 736 nW of power and requires only 0.023 mm$^2$ of area. Additionally, the amplifier has a low output impedance of 69Ω which is useful for driving low-impedance loads.

Although IOP recordings have been targeted, this research has potential use in other applications that require ultra-low-power consumption and minimal device area.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An active, implantable system for monitoring intra-ocular pressure, the system comprising:
    a capacitive sensor disposed in a sensor package configured to collect intra-ocular pressure data;
    a memory disposed to said sensor package and connected to said capacitive sensor whereby said intra-optical pressure data is continuously stored;
    a transmitter, said transmitter configured to occasionally transmit intraocular pressure data from said memory to an external receiver;
    wherein said capacitive sensor, memory, and transmitter are configured to be disposed within an eye and said external receiver is configured to be disposed outside said eye.

2. The system according to claim 1 further comprising a radio frequency receiver, configured to receive radio frequency transmissions from an external base station and convert said radio frequency transmissions into electrical current.

3. The system according to claim 2 wherein said wireless radio frequency receiver provides a radio frequency antenna, said antenna being configured for both the reception of data and the transmission of power to the wireless transceiver.

4. The system according to claim 2 further comprising a power storage capacitor charged by said electrical current and providing power to said capacitive sensor, said memory, and said transmitter.

5. The system according to claim 2 further comprising a power source configured to be charged by said electrical current and providing power to said capacitive sensor, said memory, and said transmitter.

6. The system according to claim 1, said eye is an eye of a human body.

7. The system according to claim 6, wherein said system is configured to be disposed within the suprachoroidal space of said eye of said human body.

8. The system according to claim 1 wherein said implantable system is a biocompatible package.

9. The system according to claim 8 wherein said biocompatible package is configured from a biocompatible material selected from the group of biocompatible materials consisting of ceramic, silicon, alumina, and liquid crystal polymer.

10. The system according to claim 1 further comprising a conductive polymer bonding components of said sensor package.

11. The system according to claim 1, wherein said pressure sensor is a piezoresistive micro-electro-mechanical system pressure sensor.

12. A method for monitoring intraocular pressure, said method comprising:

inserting a sensor package within an eye, said sensor package comprising a capacitive sensor, a memory, and a transmitter;

collecting continuously with said memory intraocular pressure data from said eye with said capacitive sensor;

storing said intraocular pressure data in said memory; and transmitting occasionally, via said transmitter, said intraocular pressure data from said memory to an external base unit.

13. The method according to claim 12, further comprising charging an internal power supply disposed within said sensor package, said internal power supply powering said capacitive sensor, said memory, and said transmitter.

14. The method according to claim 13, wherein said charging said internal power supply comprises transmitting a radio frequency signal to receiver disposed within said sensor package and converting said radio frequency to an electrical charge.

15. The method according to claim 13 wherein said sensor package is disposed in the suprachoroidal space of said eye.

16. The method according to claim 13 wherein said eye is a human eye.

* * * * *